(12) United States Patent
Conway et al.

(10) Patent No.: US 12,092,624 B2
(45) Date of Patent: Sep. 17, 2024

(54) AIR QUALITY SENSORS

(71) Applicant: Alarm.com Incorporated, Tysons, VA (US)

(72) Inventors: Catherine Conway, Tysons, VA (US); Robert Nathan Picardi, Herndon, VA (US); Craig Carl Heffernan, Oregon City, OR (US); Daniel Marc Goodman, Needham, MA (US); Harrison Wayne Donahue, Attleboro, MA (US)

(73) Assignee: Alarm.com Incorporated, Tysons, VA (US)

( * ) Notice: Subject to any disclaimer, the term of this patent is extended or adjusted under 35 U.S.C. 154(b) by 0 days.

(21) Appl. No.: 18/211,699

(22) Filed: Jun. 20, 2023

(65) Prior Publication Data
US 2023/0333075 A1    Oct. 19, 2023

Related U.S. Application Data

(63) Continuation of application No. 16/999,734, filed on Aug. 21, 2020.

(60) Provisional application No. 62/896,991, filed on Sep. 6, 2019.

(51) Int. Cl.
*G01N 33/00* (2006.01)
*F24F 11/62* (2018.01)
*F24F 110/72* (2018.01)

(52) U.S. Cl.
CPC .......... *G01N 33/0075* (2013.01); *F24F 11/62* (2018.01); *G01N 33/0034* (2013.01); *F24F 2110/72* (2018.01)

(58) Field of Classification Search
None
See application file for complete search history.

(56) References Cited

U.S. PATENT DOCUMENTS

| | | | |
|---|---|---|---|
| 6,782,351 B2 | 8/2004 | Reichel et al. | |
| 7,434,413 B2 | 10/2008 | Wruck | |
| 7,632,178 B2 | 12/2009 | Meneely, Jr. | |
| 9,280,884 B1 | 3/2016 | Schultz et al. | |
| 9,593,861 B1 * | 3/2017 | Burnett | F24F 11/30 |
| 10,247,434 B2 * | 4/2019 | Hrejsa | F24F 11/30 |
| 10,509,377 B2 * | 12/2019 | Willette | F24F 11/77 |
| 10,563,886 B2 | 2/2020 | McCormick | |
| 10,921,763 B1 | 2/2021 | Correnti et al. | |
| 11,226,128 B2 | 1/2022 | Morgan et al. | |
| 11,243,002 B2 | 2/2022 | Reeder | |

(Continued)

FOREIGN PATENT DOCUMENTS

FR    2988844    10/2013

*Primary Examiner* — Daniel S Larkin
(74) *Attorney, Agent, or Firm* — Fish & Richardson P.C.

(57) ABSTRACT

Methods, systems, and apparatus, including computer programs encoded on computer storage media, for integrating a monitoring system with one or more air quality sensors. The method includes receiving data indicating a level of volatile organic compounds within an area, determining an increase in the level of volatile organic compounds within the area, receiving video data that shows the area, detecting, from the video data, a new item of furniture within the area, sending a notification that indicates an increase in the level of volatile organic compounds is likely caused by the new item of furniture.

20 Claims, 4 Drawing Sheets

(56) References Cited

U.S. PATENT DOCUMENTS

| | | | |
|---|---|---|---|
| 11,686,492 B2* | 6/2023 | Ajax | F24F 8/10 705/26.7 |
| 2008/0133148 A1 | 6/2008 | Uchi et al. | |
| 2009/0053989 A1 | 2/2009 | Lunde et al. | |
| 2013/0135098 A1* | 5/2013 | Miller | G05B 15/02 324/686 |
| 2015/0077737 A1 | 3/2015 | Belinsky et al. | |
| 2016/0116181 A1 | 4/2016 | Aultman et al. | |
| 2017/0350611 A1* | 12/2017 | Su | F24F 8/80 |

* cited by examiner

AIR QUALITY SENSORS

CROSS-REFERENCE TO RELATED APPLICATION

This application is a continuation of U.S. application Ser. No. 16/999,734, filed Aug. 21, 2020, which claims the benefit of U.S. Provisional Application No. 62/896,991, filed on Sep. 6, 2019, the contents of which are incorporated by reference herein in its entirety.

TECHNICAL FIELD

This disclosure relates to property monitoring technology and, for example, integrating a monitoring system at a property with one or more air quality sensors.

BACKGROUND

Many people equip homes and businesses with monitoring systems to provide increased security for their homes and businesses. These monitoring systems include several electronic components including sensors that may detect several different activities within the monitored property.

SUMMARY

Techniques are described for monitoring technology. For example, techniques are described for integrating a monitoring system with one or more air quality sensors.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DETAILED DESCRIPTION

Indoor air quality is a chronic problem in many homes. The average adult spends eighty seven percent (87%) of their time indoors, where a lack of air circulation allows Volatile Organic Compounds (VOCs) to concentrate and cause poor air quality. This is a particular problem in modern, well-insulated homes. VOCs originate from common household products, including air fresheners, cleaning solutions, dry cleaned clothing, composite wood, paint, and furniture. VOCs that are commonly present in the home include benzene, ethylene glycol, and formaldehyde. The level of VOCs in the air can fluctuate over time and may even vary throughout the day. High concentrations of VOCs are linked to symptoms like headaches, skin and eye irritation, asthma, and fatigue.

Techniques are described for integrating a monitoring system with one or more indoor air quality sensors. The monitoring system may be configured to determine the air quality within the monitored home and provide notifications to the resident of the home indicating the air quality. The monitoring system may further be configured to automatically perform an action based on the determined air quality within the home. An Indoor Air Quality (IAQ) sensor is configured to measure ambient temperature, humidity, and total concentration level of VOCs in the air of a home equipped with an indoor quality sensor. In some examples, an indoor air quality sensor may be configured to measure specific VOC levels, particulates/particles, and pollen present in the air of a home equipped with an indoor quality sensor. The indoor air quality sensor aims to improve home health by making homeowners more aware of their air quality through monitoring and providing notifications, and by empowering homeowners to improve their air quality through setting up rules, personalized suggestions, and integrating with other devices in the monitoring ecosystem.

Figure 1:
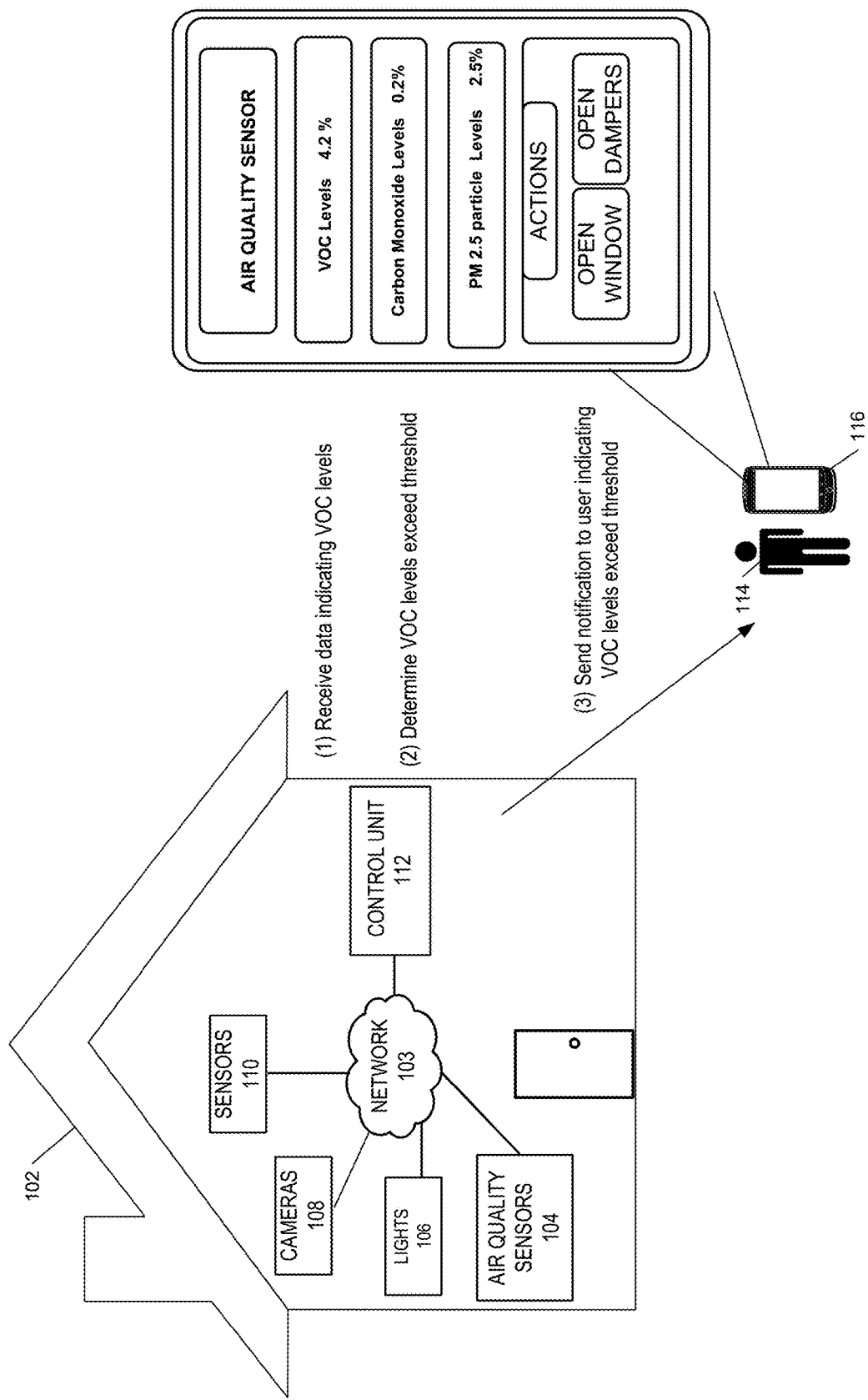
FIG. 1 illustrates an example of a monitoring system at a monitored property.

FIG. 1 illustrates an example of a monitoring system at a monitored property that is integrated with one or more air quality control sensors. As shown in FIG. 1, a property 102 (e.g. a home) of a user 114 is monitored by an in-home monitoring system (e.g., in-home security system) that includes components that are fixed within the property 102. The in-home monitoring system may include a control unit 112, one or more lights 106, one or more cameras 108, one or more sensors 110, a network 103, and one or more air quality sensors 104.

The one or more indoor air quality sensors 104 may be located throughout every room of the monitored property 102. Each of the one or more indoor air quality sensors 104 is configured to measure ambient temperature, humidity, and total concentration level of VOCs in the air of the room equipped with the sensor. Each of the one or more indoor air quality sensors 104 may be mounted to the wall of the room of the property. Each of the one or more indoor air quality sensors 104 may be battery powered. In some implementations, the one or more indoor air quality sensors 104 may be connected to a hardwired power source. In these implementations, each of the one or more sensors 104 may act as a repeating device on the network 103 to boost communication reliability. Each of the one or more sensors 104 are a small size and may be mounted in any of the one or more rooms of the property 102, and does not need to have direct interaction with the home heating, ventilation, and air conditioning (HVAC) or Air Quality management devices. The one or more indoor air quality sensors 104 may include a modular sensor cap. The modular sensor cap on each of the one or more sensors 104 is configured to allow the sensing element of the sensor to be replaced, while leaving a main portion of the sensor (main processor and radio) intact and enrolled in the network 103. In some examples, an indoor air quality sensor 104 may be configured to measure specific VOC levels, particulates, and pollen present in the air of the room equipped with the indoor quality sensor 104. In some other examples, the indoor air quality sensors 104 may be configured to detect and measure the concentration of carbon monoxide in the room equipped with the sensor. The one or more air quality control sensors 104 may communicate through Z-Wave, Bolt, Wi-Fi, Bluetooth, or any other appropriate wireless communication with the monitor control unit 112.

As illustrated in FIG. 1, the monitor control unit 112 is configured to receive data indicating the concentration levels of volatile organic compounds (VOCs) in the air of the room equipped with the sensor. In some implementations, each of the one or more air quality sensors 104 in the monitored property 102 are configured to communicate measured VOCs concentration levels to the monitor control unit 112 on a periodic basis. For example, each of the one or more air quality sensors 104 communicate the measured VOCs concentration levels to the monitor control unit 112 every sixty (60) seconds. In other implementations, each of one or more air quality sensors 104 constantly communicate measured VOCs concentration levels to the monitor control unit 112. For example, each of the one or more air quality sensors 104 communicate the measured VOCs concentration levels to the monitor control unit 112 every second. In yet another example, an air quality sensor 104 may communicate measured VOCs concentration levels to the monitor control unit 112 based on change thresholds, thereby minimizing over the air traffic and noise in the property 102.

The monitor control unit 112 compares the data indicating the concentration levels of VOCs received from the air quality sensors 104 to a threshold value of VOCs concentration levels. In some implementations, each of the one or more rooms of the monitored property 102 may have different threshold levels for VOCs concentration levels. For example, the threshold value of VOCs concentrations levels for the kitchen may be higher than the threshold value of VOCs concentration levels for the nursery. In these implementations, the threshold value of VOCs concentration levels may be a user set threshold. For example, the resident user 114 may set the threshold value of VOCs concentration for each room of the monitored property 102 through a monitoring application on a user device 116. In other implementations, the threshold value of VOCs concentration levels is set by the monitor control unit 112. In these implementations, the monitor control unit 112 may receive data from external data bases with data indicating acceptable VOCs levels. The data received from the external data bases may be based on the geographical location of the monitored property 102. For example, the data may be based on which country the monitored property 102 is located.

When the detected VOCs concentration levels for a particular room of the property 102 exceeds the threshold concentration for the room, the monitor control unit 112 communicates a notification to the user device 116 of the resident user 114. The notification may include the measured VOCs concentration levels in the particular room. In some implementations, the notification may include the last measured VOCs concentration levels from one or more other rooms in the property 102. In these implementations, the notification may include the VOCs concentration levels for the room with levels that exceed the threshold, and may include the VOCs concentration levels for the one or more surrounding rooms. For example, when the air quality sensor 104 in the kitchen determines that the detected VOCs concentration levels exceed the threshold for the kitchen, the monitor control unit 112 may communicate a notification to the user 114 indicating that the VOCs levels are exceeded in the kitchen, and including the VOC concentration levels for the living room, the dining room, and the powder room. The notification communicated to the user device 116 may also include the detected levels of carbon monoxide and particles for the particular room of the property 102.

In some implementations, the notification may include indicators which show whether the carbon monoxide levels and the particle levels in the particular room of the property are close to their threshold values. In these implementations, the user 114 sets threshold values for carbon monoxide levels and particle levels for each of the one or more rooms of the property 102. When the monitor control unit 112 detects that the VOCs concentration levels have exceeded the threshold value for a particular room, the monitor control unit 112 prompts the air quality sensor 104 located in the room to communicate the carbon monoxide levels data and particles levels data for the particular room. The monitor control unit 112 includes the carbon monoxide level and particle level data in the notification that is communicated to the resident user 114.

In some implementations, the notification may include image data of the room that is equipped with the air quality sensor 104 that detected the high level of VOCs. In these implementations, the one or more cameras 108 located in the room with the air quality sensor 104 that detects the high level of VOCs are prompted by the monitor control unit 112 to capture one or more images of the room. When the monitor control unit 112 determines that the detected VOCs concentration levels for a particular room exceeds the threshold for the particular room, the monitor control unit 112 communicates with the one or more cameras 108 in the particular room to initiate the capture of one or more images. In some examples, the monitor control unit 112 may command the one or more cameras 108 to capture images for a set time period. For example, the one or more cameras 108 may capture one or more images for thirty seconds or for sixty seconds. A video may be formed of multiple images.

In some implementations, the notification may include one or more options for actions that may be performed by the monitoring system in response to detecting that the VOCs concentration levels of a particular room exceeds the threshold. For the example illustrated in FIG. 1, the notification may include an option to open a window in the room with the high VOCs concentration levels and/or open the dampers. When the user 114 selects the option included in the notification, the monitor control unit 112 commands the system to perform the action. For example, the user 114 may select to open the window in response to detecting concentration levels of VOCs that exceeds the threshold. In some implementations, the notification may include options to switch on a fan, or to switch on an air purifier. Other options that may be included in the notification include open or close dampers, activating ventilators, sounding an alarm or turning on a light at the property 102.

In some examples, when the monitor control unit 112 determines that the detected levels of carbon monoxide in a particular room exceeds the threshold, the monitor control unit 112 may generate an audible alarm at the property 102. In these examples, the monitor control unit 112 may prompt one or more cameras 108 located in the room with the high levels of carbon monoxide to initiate the capture of video data. The monitor control unit 112 may analyze the captured video data to determine whether a human or a pet is present in the room of the property 102 with high carbon monoxide levels. In these examples, each of the one or more cameras 108 in the property 102 may include a PIR sensor and a low light sensor. The PIR sensor is configured to detect heat radiated from living objects, and a low light sensor is configured to detect movement of a living organism within the field of view of the sensor and camera lens. When the camera detects a living object is present in the room with carbon monoxide levels that exceed the threshold, the monitor control unit 112 may prompt a speaker in the room to output an audible message indicating that any one in the room should vacate immediately. In some implementations, the monitor control unit 112 automatically opens the one or more windows in the room with carbon monoxide levels that exceed the threshold. In some other implementations, the monitor control unit 112 automatically turns on an air purifier in the room with carbon monoxide levels that exceed the threshold.

The monitor control unit 112 at the property 102 may store the data received from the one or more air quality sensors 104 over a period of time. The monitor control unit 112 may utilize machine learning techniques to identify one or more patterns in the data received from the one or more air quality sensors 104 at the property 102. Based on the identified patterns in the data, the monitor control unit 112 may predict times when the VOCs concentration levels are higher at the property 102, and may automatically perform actions to prevent the VOCs concentration levels in the property 102 to exceed the threshold. For example, the monitoring control unit 112 identifies that the VOCs concentration levels measured by the air quality sensor 104 in the kitchen begins to increase on Mondays and Fridays at 1:00 PM, and meets the VOCs concentration level threshold at 2:00 PM. Based on identifying that the VOCs concentration levels begin to increase at 1:00 PM, the monitor control unit 112 commands the one or more dampers of the air purifier located in the kitchen to open at 1:00 PM on Mondays and Fridays. In some examples, the monitor control unit 112 automatically open the one or more windows in the kitchen at 1:00 PM on Mondays and Fridays.

In some implementations, the monitor control unit 112 may prompt the one or more cameras 108 in the kitchen to initiate the capture of one or more images when the VOC concentrations levels begin to rise at 1:00 PM on Mondays and Fridays. The monitor control unit 112 may identify a human in the kitchen during the periods of VOCs concentration levels. During a training period for the monitoring system, the monitor control unit 112 may communicate a notification to the user device 116 of the user 114 that includes one or more images of the human. The user 114 may respond to the notification indicating that the person is the maid, and may identify the time period as the maid's cleaning time. In these implementations, the monitor control unit 112 may initiate the capture of one or more images on Monday and Fridays at 1:00 PM. When the monitor control unit 112 does not determine the presence of a human during the time period, the monitor control unit 112 does not automatically open the dampers to the air purifier. The monitor control unit 112 may be configured to automatically open the dampers to the air purifier in the kitchen when one or more images captured from the cameras in the kitchen indicate that the maid is in the kitchen.

The user 114 may be a resident of the monitored property 102, and may set one or more thresholds for VOCs concentrations levels and particulates/particles (PM 2.5) levels for the one or more rooms equipped with air quality sensors 104 through accessing a smart home monitoring application. For example, the user 114 may set the threshold for VOCs concentration levels for the kitchen higher than the threshold for VOCs concentrations levels for the master bedroom. For another example, the user 114 may set the threshold for PM 2.5 particles levels in the hallway near the entrance of the property 102 to be higher than the threshold for PM 2.5 particles levels in the bedrooms. In some implementations, the user 114 may set the thresholds for the VOCs concentrations levels and PM 2.5 particles level to the same value for each of the rooms of the property 102. In some implementations, the monitor control unit 112 receives external data from a server that indicates safe thresholds for VOC concentrations levels and PM 2.5 particles levels. In some implementations, the external data received by the monitor control unit 112 may be data based on the geographical location of the monitored property 102.

Figure 2:
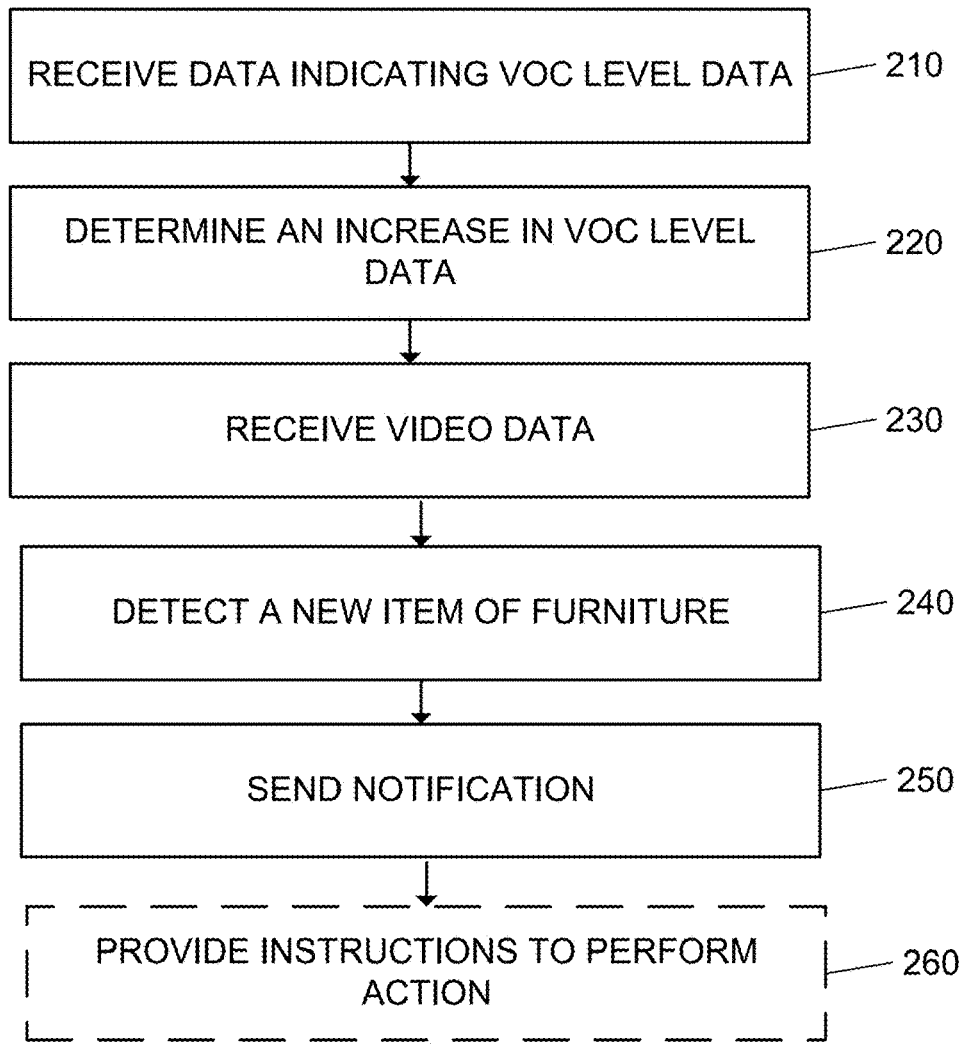
FIG. 2 is a flow chart of an example process for performing an action.

FIG. 2 is a flow chart of an example process for 200 for performing an action. The monitored property 102 may be equipped with one or more air quality sensors 104 that are located throughout the monitored property 102, and that are each configured to measure ambient temperature, humidity, and total concentration level of VOCs in the air of the property 102. The one or more air quality sensors 104 are also configured to measure specific particulates and pollen present in the air. The one or more air quality sensors 104 are also configured to detect carbon monoxide levels in the air of the property 102.

The monitor control unit 112 receives data indicating VOCs level data (210). The monitor control unit 112 may receive data indicating VOCs concentration levels on a periodic basis from the one or more air quality sensors 104 located throughout the property 102. For example, the monitor control unit 112 may receive data from the one or more air quality sensors 104 every sixty seconds. The monitor control unit 112 may receive data indicating the carbon monoxide levels, the particulates and pollen levels on a periodic basis. For example, the monitor control unit 112 may receive data indicating the carbon monoxide levels, the particulates and pollen levels every thirty seconds. Receiving data indicating a level of VOCs within an area may correspond to receiving data indicating VOCs level data. For example, the area may be a room in the property 102 and the data indicating the level of VOCs may be a parts per million reading of VOCs.

The monitor control unit 112 determines an increase in the VOCs concentration levels (220). The monitor control unit 112 may compare the data received to the previously received data to determine whether there was an increase in the VOCs concentrations levels measured by a particular sensor. In some implementations, minor changes in VOCs concentration levels may not be determined as an increase but (i) a significant change may be determined to be an increase or (ii) a change that causes the VOCs concentration levels to be greater than or equal to some threshold may be determined to be an increase.

The monitor control unit 112 receives video data (230). When the monitor control unit 112 receives data indicating that there is an increase in the VOCs concentrations, the monitor control unit 112 determines the room of the property 102 with the elevated VOCs concentration levels. The monitor control unit 112 then commands the one or more cameras 108 that are located in the room of the property 102 with the elevated levels to initiate the capture of one or more images of the room. For example, when the air quality sensor 104 in the living room detects an elevated level of VOCs concentrations, the monitor control unit 112 commands the one or more cameras 108 in the living room to capture images. The one or more cameras 108 may be pan/tilt cameras that are configured to pan or tilt to change the field of view of the camera to ensure that the one or more captured images include each square inch of the room with the elevated VOCs concentration levels.

In some implementations, receiving video data that shows the area includes, in response to the determination of the increase in the level of VOCs within the area, provide a command to a camera 108 to capture an image of the area and receiving, from the camera 108, the image of the area in response to the command. For example, the monitor control unit 112 may not be receiving video from a camera, of the cameras 108, that is in the room and, in response to the control unit 112 determining the increase in the level of VOCs within the area, the control unit 112 may provide an instruction to the camera to capture an image and then receives the image from the camera.

In some implementations, receiving video data that shows the area includes continuously receiving the video data from a camera that views the area. For example, the monitor control unit 112 may continuously receive an image every five seconds from a camera that views the area whether or not an increase in VOCs level is detected in the area.

The monitor control unit 112 detects a new item of furniture (240). The monitor control unit 112 receives the image data from the one or more cameras 108, and analyzes the one or more images. The monitor control unit 112 may determine, based on using one or more different analytical techniques that a new item presence in the room coincides with the increase in the VOCs levels in the particular room.

In some implementations, detecting, from the video data, a new item of furniture within the area may include determining that the new item of furniture is shown in the video data and is not shown in an image of the area that was captured before the video data was captured. For example, the monitor control unit 112 may compare the image data to one or more captured images of the room. The one or more captured images may be captured during the initial configuration of the monitoring system and/or captured a few seconds, minutes, hours, or some other amount of time before the new item of furniture was added to the area. For example, when the resident user 114 has a new couch delivered to the monitored property 102 and placed in the living room, the monitor control unit 112 may detect the new couch from the one or more images of the living room. In another example, the captured images may have been captured from a day before the increase in VOCs was detected. The monitor control unit 112 sends a notification to the resident user 114 (250). The notification may be communicated to the user device 116 of the user 114. For example, the notification may be sent as an SMS message, or an in-app message through the smart home monitoring application. The notification may notify the user 114 that the elevated VOCs concentration levels have been detected, and may include the location of the air quality sensor 104 that detected the elevated VOCs concentration levels. In some implementations, the notification may include the one or more captured images of the room.

In some implementations, sending a notification that indicates an increase in the level of VOCs is likely caused by the new item of furniture includes determining that the new item of furniture within the area was added at a time that corresponds to when the level of VOCs within the area was determined to increase and, in response to determining that the new item of furniture within the area was added at the time that corresponds to when the level of VOCs within the area was determined to increase, sending the notification. For example, the control unit 112 may determine that the new item of furniture was added within a few seconds, minutes, or some other amount of time that the increase in the level of VOCs within the area was determined and, in response, sending the notification that the increase in the level of VOCs is likely caused by the new item of furniture. In another example, the control unit 112 may determine that the new item of furniture was not added within a few seconds, minutes, or some other amount of time that the increase in the level of VOCs within the area was determined and, in response, not send the notification that the increase in the level of VOCs is likely caused by the new item of furniture and instead send a notification that there was an increase in the level of VOCs for an unknown reason.

In some implementations sending a notification that indicates an increase in the level of VOCs is likely caused by the new item of furniture includes providing a textual indication that the level of VOCs has increased and an image of the new item of furniture. For example, the control unit 112 may send a message that includes both text of "Increase in VOCs level detected in family room and is likely caused by the new furniture shown below" and an image of the new item of furniture.

The monitor control unit 112 provides instructions to perform an action (260). For example, the control unit 112 may provide an instruction to a HVAC system to ventilate the area. In some implementations, the monitor control unit 112 automatically provides instructions to perform an action in response to detecting a new item of furniture in the room of the property 102 with the elevated VOCs concentration levels. In these implementations, the user 114 may access the smart home monitoring application to indicate the action that should be performed during the configuration of the monitoring system. For example, the user 114 may set the action to be performed when VOCs levels are elevated in the kitchen as opening the one or more windows in the living room. For another example, the user 114 may set the action to be performed with the particulate levels are elevated in the bedroom as opening the dampers of the one or more air purifiers in the bedroom. In another example, the user 114 may set the action to be performed when VOCs levels are elevated in the living room as switching on a fan and opening the one or more windows in the living room. In some implementations, the notification that is communicated to the user 114 may request the user to identify which action should be performed. For example, the notification may request whether to open the windows, switch on a fan, or open the one or more dampers of the air purifier in the room with the elevated levels.

When the elevated VOCs concentration levels occur when a new item of furniture is detected, the monitor control unit 112 may automatically provide instruction to the windows in the living room to open. The monitor control unit 112 may communicate wirelessly with the smart windows in the monitored property 102 to automatically open the windows in the living room.

In some implementations, the process 200 may include actions of determining a second increase in the level of VOCs within the area, receiving second video data that shows the area, detecting, from the second video data, a new item of furniture is not within the area, determining a third increase in the level of VOCs within the area, receiving third video data that shows the area, detecting, from the third video data, a new item of furniture is not within the area, and providing, based on both when the second increase occurred and when the third increase occurred, an instruction to a heating, ventilation, and air conditioning system to ventilate the area. For example, a resident of a home may begin cleaning their kitchen floor every day at 1 PM using a new cleaning solution that releases VOCs. Accordingly in the example, the control unit 112 may determine during a first day that an increase in VOCs was detected in the kitchen but a new item of furniture was not added to the kitchen, then determine this happened again the next day, and, in response, determine that VOCs is likely to increase around the same time the next day in the kitchen and instruct a HVAC system to begin ventilating the kitchen around that time the next day before an increase in VOCs is detected.

In some implementations, the process 200 may include actions of determining a second increase in the level of VOCs within the area, receiving second video data that shows the area, detecting, from the second video data, a new item of furniture is not within the area, determining that a timing of the second increase corresponds to occupancy in the area, and providing an indication to clean the area. For example, the carpets in a living room may become so dirty that the carpets start releasing large amounts of VOCs when people walk on the carpets. In the example, the control unit 112 may determine that no item of furniture was newly added to the living room but video shows a person started walking on the carpets in the living room when the increase in VOCs was detected and, in response, provide an alert of "A VOCs increase has been detected in the living room that may be caused by the carpet being dirty. Cleaning the carpet may reduce VOCs."

Figure 3:
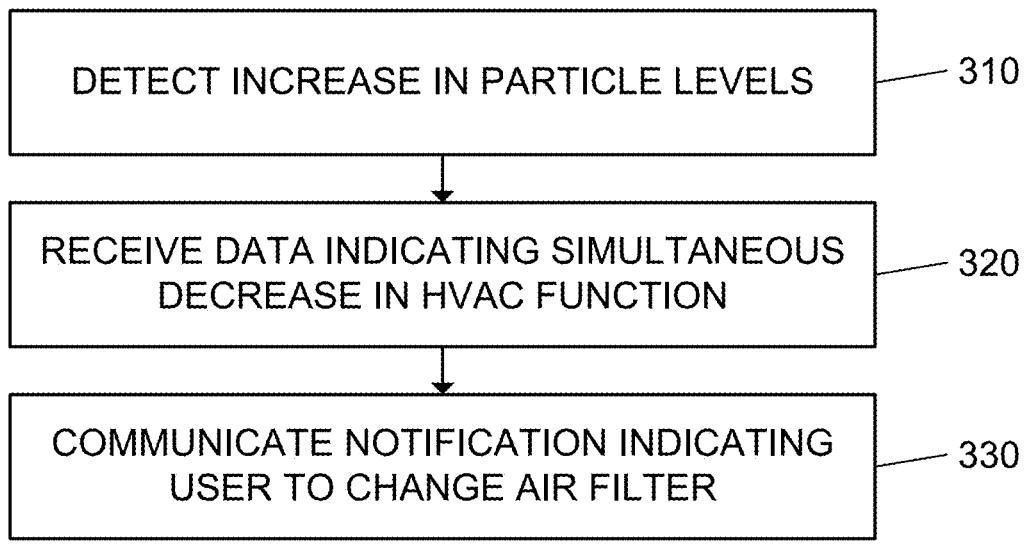
FIG. 3 is a flow chart of an example process for communicating a notification to a user.

FIG. 3 is a flow chart of an example process 300 for communicating a notification to a user 114. An air quality sensor 104 detects an increase in the particle levels at a room of the property 102 (310). The air quality sensor is configured to measure ambient temperature, humidity, total concentration level of VOCs, specific particulates and pollen present in the air. The one or more air quality sensors 104 are also configured to detect carbon monoxide levels in the air of the property 102.

The monitor control unit 112 receives data indicating a simultaneous decrease in HVAC function (320). The monitor control unit 112 may receive data from the HVAC system at the monitored property 102 periodically. For example, the monitor control unit 112 may receive data from the HVAC system every sixty seconds. The monitor control unit 112 may utilize one or more different techniques to analyze the thermostat analytics data received from the HVAC system. Based on analyzing the thermostat analytics data received from the HVAC system and the data received from the one or more air quality sensors 104, the monitor control unit 112 may identify that the increase in particles occurs simultaneously with the decrease in the HVAC function.

The monitor control unit 112 communicates a notification to the user 114 indicating that the air filter should be changed (330). In some implementations, the notification may be communicated as an SMS message or as an in-app message through the smart home monitoring application. In some implementations, the notification may be an audible alarm that is emitted from the HVAC control panel. In some implementations, the monitor control unit 112 may indicate the type of filter that should be used. For example, when the monitor control unit 112 determines that there are high levels of pollen in the air of the property 102, the monitor control unit 112 may indicate that a pollen reducing air filter be used in the HVAC system.

In some implementations, when the user 114 does not change the air filter within a set period of time, the monitor control unit 112 may control switch on the one or more air purifiers located throughout the monitored property 102. For example, when the user 114 has not changed the air filter within forty eight (48) hours after receiving a notification to change the filter, the monitor control unit 112 may switch on one or more air purifiers. In some implementations, the monitor control unit 112 may switch on one or more air purifiers in the one or more rooms of the house with the poorest air quality. For example, the monitor control unit 112 may switch on the one or more air purifiers in the kitchen and the bedroom.

Figure 4:
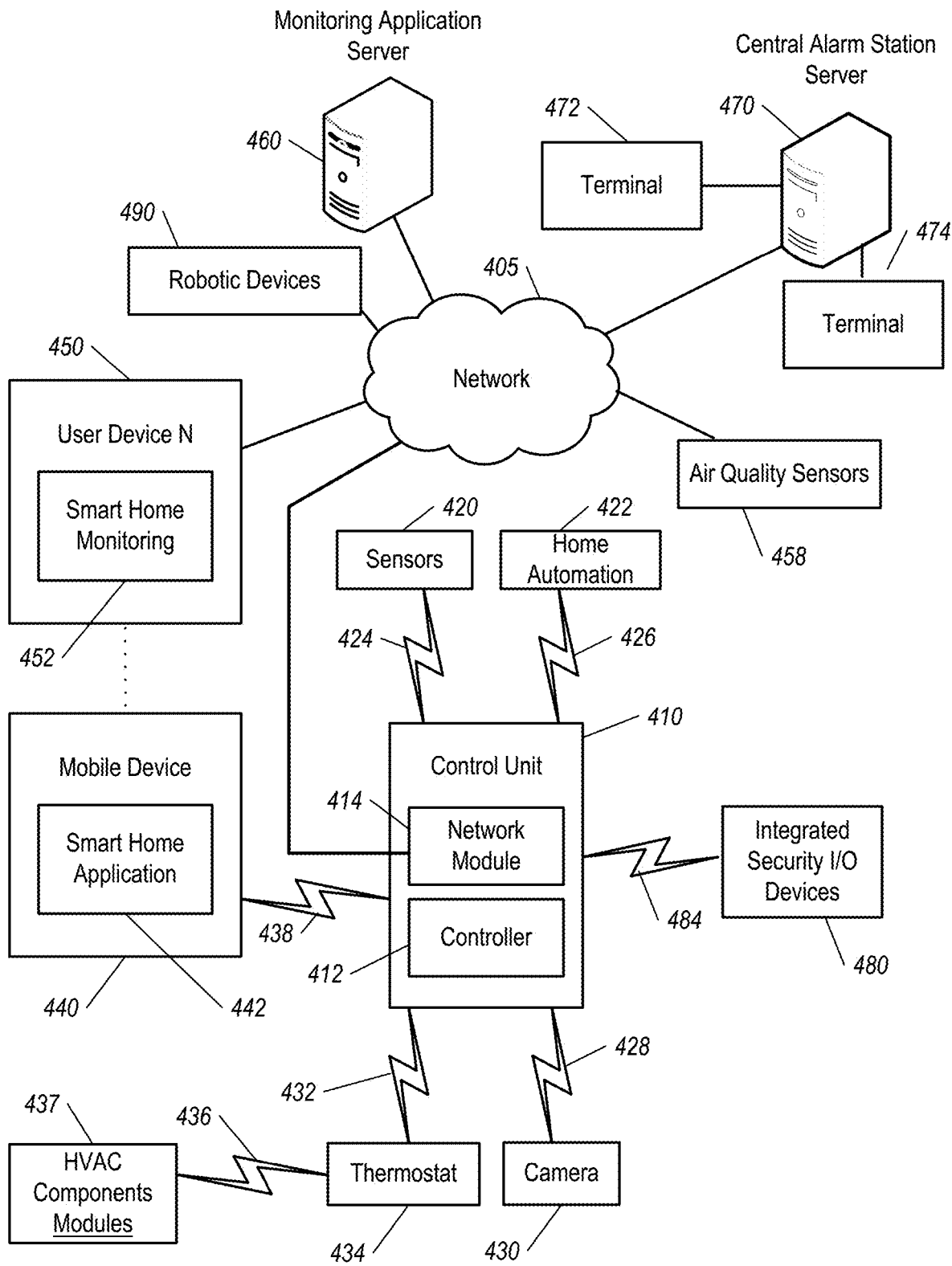
FIG. 4 illustrates an example of a monitoring system integrated with one or more smart air quality sensors.

FIG. 4 is a diagram illustrating an example of a home monitoring system 400. The electronic system 400 includes a network 405, a control unit 410, one or more user devices 440 and 450, a monitoring server 460, and a central alarm station server 470. In some examples, the network 405 facilitates communications between the control unit 410, the one or more user devices 440 and 450, the monitoring server 460, and the central alarm station server 470.

The network 405 is configured to enable exchange of electronic communications between devices connected to the network 405. For example, the network 405 may be configured to enable exchange of electronic communications between the control unit 410, the one or more user devices 440 and 450, the monitoring server 460, and the central alarm station server 470. The network 405 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 405 may include multiple networks or subnetworks, each of which may include, for example, a wired or wireless data pathway. The network 405 may include a circuit-switched network, a packet-switched data network, or any other network able to carry electronic communications (e.g., data or voice communications). For example, the network 405 may include networks based on the Internet protocol (IP), asynchronous transfer mode (ATM), the PSTN, packet-switched networks based on IP, X.25, or Frame Relay, or other comparable technologies and may support voice using, for example, VOIP, or other comparable protocols used for voice communications. The network 405 may include one or more networks that include wireless data channels and wireless voice channels. The network 405 may be a wireless network, a broadband network, or a combination of networks including a wireless network and a broadband network.

The control unit 410 includes a controller 412 and a network module 414. The controller 412 is configured to control a control unit monitoring system (e.g., a control unit system) that includes the control unit 410. In some examples, the controller 412 may include a processor or other control circuitry configured to execute instructions of a program that controls operation of a control unit system. In these examples, the controller 412 may be configured to receive input from sensors, flow meters, or other devices included in the control unit system and control operations of devices included in the household (e.g., speakers, lights, doors, etc.). For example, the controller 412 may be configured to control operation of the network module 414 included in the control unit 410.

The network module 414 is a communication device configured to exchange communications over the network 405. The network module 414 may be a wireless communication module configured to exchange wireless communications over the network 405. For example, the network module 414 may be a wireless communication device configured to exchange communications over a wireless data channel and a wireless voice channel. In this example, the network module 414 may transmit alarm data over a wireless data channel and establish a two-way voice communication session over a wireless voice channel. The wireless communication device may include one or more of a LTE module, a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 414 also may be a wired communication module configured to exchange communications over the network 405 using a wired connection. For instance, the network module 414 may be a modem, a network interface card, or another type of network interface device. The network module 414 may be an Ethernet network card configured to enable the control unit 410 to communicate over a local area network and/or the Internet. The network module 414 also may be a voice band modem configured to enable the alarm panel to communicate over the telephone lines of Plain Old Telephone Systems (POTS).

The control unit system that includes the control unit 410 includes one or more sensors. For example, the monitoring system may include multiple sensors 420. The sensors 420 may include a lock sensor, a contact sensor, a motion sensor, or any other type of sensor included in a control unit system. The sensors 420 also may include an environmental sensor, such as a temperature sensor, a water sensor, a rain sensor, a wind sensor, a light sensor, a smoke detector, a carbon monoxide detector, an air quality sensor, etc. The sensors 420 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some examples, the health monitoring sensor can be a wearable sensor that attaches to a user in the home. The health monitoring sensor can collect various health data, including pulse, heart-rate, respiration rate, sugar or glucose level, bodily temperature, or motion data. The sensors 420 can also include a radio-frequency identification (RFID) sensor that identifies a particular article that includes a pre-assigned RFID tag.

The control unit 410 communicates with the home automation controls 422 and a camera 430 to perform monitoring. The home automation controls 422 are connected to one or more devices that enable automation of actions in the home. For instance, the home automation controls 422 may be connected to one or more lighting systems and may be configured to control operation of the one or more lighting systems. Also, the home automation controls 422 may be connected to one or more electronic locks at the home and may be configured to control operation of the one or more electronic locks (e.g., control Z-Wave locks using wireless communications in the Z-Wave protocol). Further, the home automation controls 422 may be connected to one or more appliances at the home and may be configured to control operation of the one or more appliances. The home automation controls 422 may include multiple modules that are each specific to the type of device being controlled in an automated manner. The home automation controls 422 may control the one or more devices based on commands received from the control unit 410. For instance, the home automation controls 422 may cause a lighting system to illuminate an area to provide a better image of the area when captured by a camera 430.

The camera 430 may be a video/photographic camera or other type of optical sensing device configured to capture images. For instance, the camera 430 may be configured to capture images of an area within a building or home monitored by the control unit 410. The camera 430 may be configured to capture single, static images of the area and also video images of the area in which multiple images of the area are captured at a relatively high frequency (e.g., thirty images per second). The camera 430 may be controlled based on commands received from the control unit 410.

The camera 430 may be triggered by several different types of techniques. For instance, a Passive Infra-Red (PIR) motion sensor may be built into the camera 430 and used to trigger the camera 430 to capture one or more images when motion is detected. The camera 430 also may include a microwave motion sensor built into the camera and used to trigger the camera 430 to capture one or more images when motion is detected. The camera 430 may have a "normally open" or "normally closed" digital input that can trigger capture of one or more images when external sensors (e.g., the sensors 420, PIR, door/window, etc.) detect motion or other events. In some implementations, the camera 430 receives a command to capture an image when external devices detect motion or another potential alarm event. The camera 430 may receive the command from the controller 412 or directly from one of the sensors 420. In some examples, the camera 430 triggers integrated or external illuminators (e.g., Infra-Red, Z-wave controlled "white" lights, lights controlled by the home automation controls 422, etc.) to improve image quality when the scene is dark. An integrated or separate light sensor may be used to determine if illumination is desired and may result in increased image quality.

The camera 430 may be programmed with any combination of time/day schedules, system "arming state", or other variables to determine whether images should be captured or not when triggers occur. The camera 430 may enter a low-power mode when not capturing images. In this case, the camera 430 may wake periodically to check for inbound messages from the controller 412. The camera 430 may be powered by internal, replaceable batteries if located remotely from the control unit 410. The camera 430 may employ a small solar cell to recharge the battery when light is available. Alternatively, the camera 430 may be powered by the controller's 412 power supply if the camera 430 is co-located with the controller 412. In some implementations, the camera 430 communicates directly with the monitoring server 460 over the Internet. In these implementations, image data captured by the camera 430 does not pass through the control unit 410 and the camera 430 receives commands related to operation from the monitoring server 460.

The system 400 also includes thermostat 434 to perform dynamic environmental control at the home. The thermostat 434 is configured to monitor temperature and/or energy consumption of an HVAC system associated with the thermostat 434, and is further configured to provide control of environmental (e.g., temperature) settings. In some implementations, the thermostat 434 can additionally or alternatively receive data relating to activity at a home and/or environmental data at a home, e.g., at various locations indoors and outdoors at the home. The thermostat 434 can directly measure energy consumption of the HVAC system associated with the thermostat, or can estimate energy consumption of the HVAC system associated with the thermostat 434, for example, based on detected usage of one or more components of the HVAC system associated with the thermostat 434. The thermostat 434 can communicate temperature and/or energy monitoring information to or from the control unit 410 and can control the environmental (e.g., temperature) settings based on commands received from the control unit 410.

In some implementations, the thermostat 434 is a dynamically programmable thermostat and can be integrated with the control unit 410. For example, the dynamically programmable thermostat 434 can include the control unit 410, e.g., as an internal component to the dynamically programmable thermostat 434. In addition, the control unit 410 can be a gateway device that communicates with the dynamically programmable thermostat 434. In some implementations, the thermostat 434 is controlled via one or more home automation controls 422.

A module 437 is connected to one or more components of an HVAC system associated with a home, and is configured to control operation of the one or more components of the HVAC system. In some implementations, the module 437 is also configured to monitor energy consumption of the HVAC system components, for example, by directly measuring the energy consumption of the HVAC system components or by estimating the energy usage of the one or more HVAC system components based on detecting usage of components of the HVAC system. The module 437 can communicate energy monitoring information and the state of the HVAC system components to the thermostat 434 and can control the one or more components of the HVAC system based on commands received from the thermostat 434.

The system 400 includes one or more smart air quality sensors 458. The one or more air quality sensors 458 are mounted to the walls of one or more rooms through the monitored property 102. Each of the one or more air quality sensors are configured to measure ambient temperature, humidity, and total concentration level of VOCs in the air of a home equipped with an indoor quality sensor. In some examples, an indoor air quality sensor may be configured to measure specific VOC levels, particulates, and pollen present in the air of a home equipped with an indoor quality sensor. The one or more air quality sensors 458 are configured to communicate with the control unit 410 at the monitored property.

In some examples, the system 400 further includes one or more robotic devices 490. The robotic devices 490 may be any type of robots that are capable of moving and taking actions that assist in home monitoring. For example, the robotic devices 490 may include drones that are capable of moving throughout a home based on automated control technology and/or user input control provided by a user. In this example, the drones may be able to fly, roll, walk, or otherwise move about the home. The drones may include helicopter type devices (e.g., quad copters), rolling helicopter type devices (e.g., roller copter devices that can fly and also roll along the ground, walls, or ceiling) and land vehicle type devices (e.g., automated cars that drive around a home). In some cases, the robotic devices 490 may be robotic devices 490 that are intended for other purposes and merely associated with the system 400 for use in appropriate circumstances. For instance, a robotic vacuum cleaner device may be associated with the monitoring system 400 as one of the robotic devices 490 and may be controlled to take action responsive to monitoring system events.

In some examples, the robotic devices 490 automatically navigate within a home. In these examples, the robotic devices 490 include sensors and control processors that guide movement of the robotic devices 490 within the home. For instance, the robotic devices 490 may navigate within the home using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about a space. The robotic devices 490 may include control processors that process output from the various sensors and control the robotic devices 490 to move along a path that reaches the desired destination and avoids obstacles. In this regard, the control processors detect walls or other obstacles in the home and guide movement of the robotic devices 490 in a manner that avoids the walls and other obstacles.

In addition, the robotic devices 490 may store data that describes attributes of the home. For instance, the robotic devices 490 may store a floorplan and/or a three-dimensional model of the home that enables the robotic devices 490 to navigate the home. During initial configuration, the robotic devices 490 may receive the data describing attributes of the home, determine a frame of reference to the data (e.g., a home or reference location in the home), and navigate the home based on the frame of reference and the data describing attributes of the home. Further, initial configuration of the robotic devices 490 also may include learning of one or more navigation patterns in which a user provides input to control the robotic devices 490 to perform a specific navigation action (e.g., fly to an upstairs bedroom and spin around while capturing video and then return to a home charging base). In this regard, the robotic devices 490 may learn and store the navigation patterns such that the robotic devices 490 may automatically repeat the specific navigation actions upon a later request.

In some examples, the robotic devices 490 may include data capture and recording devices. In these examples, the robotic devices 490 may include one or more cameras, one or more motion sensors, one or more microphones, one or more biometric data collection tools, one or more temperature sensors, one or more humidity sensors, one or more air flow sensors, and/or any other types of sensors that may be useful in capturing monitoring data related to the home and users in the home. The one or more biometric data collection tools may be configured to collect biometric samples of a person in the home with or without contact of the person. For instance, the biometric data collection tools may include a fingerprint scanner, a hair sample collection tool, a skin cell collection tool, and/or any other tool that allows the robotic devices 490 to take and store a biometric sample that can be used to identify the person (e.g., a biometric sample with DNA that can be used for DNA testing). In some implementations, the robotic devices 490 may include output devices. In these implementations, the robotic devices 490 may include one or more displays, one or more speakers, and/or any type of output devices that allow the robotic devices 490 to communicate information to a nearby user.

The robotic devices 490 also may include a communication module that enables the robotic devices 490 to communicate with the control unit 410, each other, and/or other devices. The communication module may be a wireless communication module that allows the robotic devices 490 to communicate wirelessly. For instance, the communication module may be a Wi-Fi module that enables the robotic devices 490 to communicate over a local wireless network at the home. The communication module further may be a 900 MHz wireless communication module that enables the robotic devices 490 to communicate directly with the control unit 410. Other types of short-range wireless communication protocols, such as Bluetooth, Bluetooth LE, Z-wave, Zigbee, etc., may be used to allow the robotic devices 490 to communicate with other devices in the home. In some implementations, the robotic devices 490 may communicate with each other or with other devices of the system 400 through the network 405.

The robotic devices 490 further may include processor and storage capabilities. The robotic devices 490 may include any suitable processing devices that enable the robotic devices 490 to operate applications and perform the actions described throughout this disclosure. In addition, the robotic devices 490 may include solid state electronic storage that enables the robotic devices 490 to store applications, configuration data, collected sensor data, and/or any other type of information available to the robotic devices 490.

The robotic devices 490 are associated with one or more charging stations. The charging stations may be located at predefined home base or reference locations in the home. The robotic devices 490 may be configured to navigate to the charging stations after completion of tasks needed to be performed for the monitoring system 400. For instance, after completion of a monitoring operation or upon instruction by the control unit 410, the robotic devices 490 may be configured to automatically fly to and land on one of the charging stations. In this regard, the robotic devices 490 may automatically maintain a fully charged battery in a state in which the robotic devices 490 are ready for use by the monitoring system 400.

The charging stations may be contact based charging stations and/or wireless charging stations. For contact based charging stations, the robotic devices 490 may have readily accessible points of contact that the robotic devices 490 are capable of positioning and mating with a corresponding contact on the charging station. For instance, a helicopter type robotic device may have an electronic contact on a portion of its landing gear that rests on and mates with an electronic pad of a charging station when the helicopter type robotic device lands on the charging station. The electronic contact on the robotic device may include a cover that opens to expose the electronic contact when the robotic device is charging and closes to cover and insulate the electronic contact when the robotic device is in operation.

For wireless charging stations, the robotic devices 490 may charge through a wireless exchange of power. In these cases, the robotic devices 490 need only locate themselves closely enough to the wireless charging stations for the wireless exchange of power to occur. In this regard, the positioning needed to land at a predefined home base or reference location in the home may be less precise than with a contact based charging station. Based on the robotic devices 490 landing at a wireless charging station, the wireless charging station outputs a wireless signal that the robotic devices 490 receive and convert to a power signal that charges a battery maintained on the robotic devices 490.

In some implementations, each of the robotic devices 490 has a corresponding and assigned charging station such that the number of robotic devices 490 equals the number of charging stations. In these implementations, the robotic devices 490 always navigate to the specific charging station assigned to that robotic device. For instance, a first robotic device may always use a first charging station and a second robotic device may always use a second charging station. In some examples, the robotic devices 490 may share charging stations. For instance, the robotic devices 490 may use one or more community charging stations that are capable of charging multiple robotic devices 490. The community charging station may be configured to charge multiple robotic devices 490 in parallel. The community charging station may be configured to charge multiple robotic devices 490 in serial such that the multiple robotic devices 490 take turns charging and, when fully charged, return to a predefined home base or reference location in the home that is not associated with a charger. The number of community charging stations may be less than the number of robotic devices 490. Also, the charging stations may not be assigned to specific robotic devices 490 and may be capable of charging any of the robotic devices 490. In this regard, the robotic devices 490 may use any suitable, unoccupied charging station when not in use. For instance, when one of the robotic devices 490 has completed an operation or is in need of battery charge, the control unit 410 references a stored table of the occupancy status of each charging station and instructs the robotic device to navigate to the nearest charging station that is unoccupied.

The system 400 further includes one or more integrated security devices 480. The one or more integrated security devices may include any type of device used to provide alerts based on received sensor data. For instance, the one or more control units 410 may provide one or more alerts to the one or more integrated security input/output devices 480. Additionally, the one or more control units 410 may receive one or more sensor data from the sensors 420 and determine whether to provide an alert to the one or more integrated security input/output devices 480.

The sensors 420, the home automation controls 422, the camera 430, the thermostat 434, the one or more user devices 440 and 450, and the integrated security devices 480 may communicate with the controller 412 over communication links 424, 426, 428, 432, 436, 438, and 484. The communication links 424, 426, 428, 432, 436, 438, and 484 may be a wired or wireless data pathway configured to transmit signals from the sensors 420, the home automation controls 422, the camera 430, the thermostat 434, the one or more user devices 440 and 450, and the integrated security devices 480 to the controller 412. The sensors 420, the home automation controls 422, the camera 430, the thermostat 434, the one or more user devices 440 and 450, and the integrated security devices 480 may continuously transmit sensed values to the controller 412, periodically transmit sensed values to the controller 412, or transmit sensed values to the controller 412 in response to a change in a sensed value. The user devices 440, 450 may communicate with the control unit 410 via the communication link 438.

The communication links 424, 426, 428, 432, 436, 438, and 484 may include a local network. The sensors 420, the home automation controls 422, the camera 430, the thermostat 434, the one or more user devices 440 and 450, and the integrated security devices 480, and the controller 412 may exchange data and commands over the local network. The local network may include 802.11 "Wi-Fi" wireless Ethernet (e.g., using low-power Wi-Fi chipsets), Z-Wave, Zigbee, Bluetooth, "Homeplug" or other "Powerline" networks that operate over AC wiring, and a Category 5 (CAT5) or Category 6 (CAT6) wired Ethernet network. The local network may be a mesh network constructed based on the devices connected to the mesh network.

The monitoring server 460 is an electronic device configured to provide monitoring services by exchanging electronic communications with the control unit 410, the one or more user devices 440 and 450, and the central alarm station server 470 over the network 405. For example, the monitoring server 460 may be configured to monitor events (e.g., alarm events) generated by the control unit 410. In this example, the monitoring server 460 may exchange electronic communications with the network module 414 included in the control unit 410 to receive information regarding events (e.g., alerts) detected by the control unit 410. The monitoring server 460 also may receive information regarding events (e.g., alerts) from the one or more user devices 440 and 450. In some examples, the monitoring server 460 may route alert data received from the network module 414 or the one or more user devices 440 and 450 to the central alarm station server 470. For example, the monitoring server 460 may transmit the alert data to the central alarm station server 470 over the network 405.

The monitoring server 460 may store sensor and image data received from the monitoring system and perform analysis of sensor and image data received from the monitoring system. Based on the analysis, the monitoring server 460 may communicate with and control aspects of the control unit 410 or the one or more user devices 440 and 450. The monitoring server 460 may provide various monitoring services to the system 400. For example, the monitoring server 460 may analyze the sensor, image, and other data to determine an activity pattern of a resident of the home monitored by the system 400. In some implementations, the monitoring server 460 may analyze the data for alarm conditions or may determine and perform actions at the home by issuing commands to one or more of the controls 422, possibly through the control unit 410.

The central alarm station server 470 is an electronic device configured to provide alarm monitoring service by exchanging communications with the control unit 410, the one or more mobile devices 440 and 450, and the monitoring server 460 over the network 405. For example, the central alarm station server 470 may be configured to monitor alerting events generated by the control unit 410. In this example, the central alarm station server 470 may exchange communications with the network module 414 included in the control unit 410 to receive information regarding alerting events detected by the control unit 410. The central alarm station server 470 also may receive information regarding alerting events from the one or more mobile devices 440 and 450 and/or the monitoring server 460.

The central alarm station server 470 is connected to multiple terminals 472 and 474. The terminals 472 and 474 may be used by operators to process alerting events. For example, the central alarm station server 470 may route alerting data to the terminals 472 and 474 to enable an operator to process the alerting data. The terminals 472 and 474 may include general-purpose computers (e.g., desktop personal computers, workstations, or laptop computers) that are configured to receive alerting data from a server in the central alarm station server 470 and render a display of information based on the alerting data. For instance, the controller 412 may control the network module 414 to transmit, to the central alarm station server 470, alerting data indicating that a sensor 420 detected motion from a motion sensor via the sensors 420. The central alarm station server 470 may receive the alerting data and route the alerting data to the terminal 472 for processing by an operator associated with the terminal 472. The terminal 472 may render a display to the operator that includes information associated with the alerting event (e.g., the lock sensor data, the motion sensor data, the contact sensor data, etc.) and the operator may handle the alerting event based on the displayed information. In some implementations, the terminals 472 and 474 may be mobile devices or devices designed for a specific function. Although FIG. 4 illustrates two terminals for brevity, actual implementations may include more (and, perhaps, many more) terminals.

The one or more authorized user devices 440 and 450 are devices that host and display user interfaces. For instance, the user device 440 is a mobile device that hosts or runs one or more native applications (e.g., the smart home application 442). The user device 440 may be a cellular phone or a non-cellular locally networked device with a display. The user device 440 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 440 may perform functions unrelated to the monitoring system, such as placing personal telephone calls, playing music, playing video, displaying pictures, browsing the Internet, maintaining an electronic calendar, etc.

The user device 440 includes a smart home application 442. The smart home application 442 refers to a software/firmware program running on the corresponding mobile device that enables the user interface and features described throughout. The user device 440 may load or install the smart home application 442 based on data received over a network or data received from local media. The smart home application 442 runs on mobile devices platforms, such as iPhone, iPod touch, Blackberry, Google Android, Windows Mobile, etc. The smart home application 442 enables the user device 440 to receive and process image and sensor data from the monitoring system.

The user device 450 may be a general-purpose computer (e.g., a desktop personal computer, a workstation, or a laptop computer) that is configured to communicate with the monitoring server 460 and/or the control unit 410 over the network 405. The user device 450 may be configured to display a smart home user interface 452 that is generated by the user device 450 or generated by the monitoring server 460. For example, the user device 450 may be configured to display a user interface (e.g., a web page) provided by the monitoring server 460 that enables a user to perceive images captured by the camera 430 and/or reports related to the monitoring system. Although FIG. 4 illustrates two user devices for brevity, actual implementations may include more (and, perhaps, many more) or fewer user devices.

In some implementations, the one or more user devices 440 and 450 communicate with and receive monitoring system data from the control unit 410 using the communication link 438. For instance, the one or more user devices 440 and 450 may communicate with the control unit 410 using various local wireless protocols such as Wi-Fi, Bluetooth, Z-wave, Zigbee, HomePlug (ethernet over power line), or wired protocols such as Ethernet and USB, to connect the one or more user devices 440 and 450 to local security and automation equipment. The one or more user devices 440 and 450 may connect locally to the monitoring system and its sensors and other devices. The local connection may improve the speed of status and control communications because communicating through the network 405 with a remote server (e.g., the monitoring server 460) may be significantly slower.

Although the one or more user devices 440 and 450 are shown as communicating with the control unit 410, the one or more user devices 440 and 450 may communicate directly with the sensors and other devices controlled by the control unit 410. In some implementations, the one or more user devices 440 and 450 replace the control unit 410 and perform the functions of the control unit 410 for local monitoring and long range/offsite communication.

In other implementations, the one or more user devices 440 and 450 receive monitoring system data captured by the control unit 410 through the network 405. The one or more user devices 440, 450 may receive the data from the control unit 410 through the network 405 or the monitoring server 460 may relay data received from the control unit 410 to the one or more user devices 440 and 450 through the network 405. In this regard, the monitoring server 460 may facilitate communication between the one or more user devices 440 and 450 and the monitoring system.

In some implementations, the one or more user devices 440 and 450 may be configured to switch whether the one or more user devices 440 and 450 communicate with the control unit 410 directly (e.g., through link 438) or through the monitoring server 460 (e.g., through network 405) based on a location of the one or more user devices 440 and 450. For instance, when the one or more user devices 440 and 450 are located close to the control unit 410 and in range to communicate directly with the control unit 410, the one or more user devices 440 and 450 use direct communication. When the one or more user devices 440 and 450 are located far from the control unit 410 and not in range to communicate directly with the control unit 410, the one or more user devices 440 and 450 use communication through the monitoring server 460.

Although the one or more user devices 440 and 450 are shown as being connected to the network 405, in some implementations, the one or more user devices 440 and 450 are not connected to the network 405. In these implementations, the one or more user devices 440 and 450 communicate directly with one or more of the monitoring system components and no network (e.g., Internet) connection or reliance on remote servers is needed.

In some implementations, the one or more user devices 440 and 450 are used in conjunction with only local sensors and/or local devices in a house. In these implementations, the system 400 includes the one or more user devices 440 and 450, the sensors 420, the home automation controls 422, the camera 430, and the robotic devices 490. The one or more user devices 440 and 450 receive data directly from the sensors 420, the home automation controls 422, the camera 430, and the robotic devices 490 and sends data directly to the sensors 420, the home automation controls 422, the camera 430, and the robotic devices 490. The one or more user devices 440, 450 provide the appropriate interfaces/ processing to provide visual surveillance and reporting.

In other implementations, the system 400 further includes network 405 and the sensors 420, the home automation controls 422, the camera 430, the thermostat 434, and the robotic devices 490 are configured to communicate sensor and image data to the one or more user devices 440 and 450 over network 405 (e.g., the Internet, cellular network, etc.). In yet another implementation, the sensors 420, the home automation controls 422, the camera 430, the thermostat 434, and the robotic devices 490 are intelligent enough to change the communication pathway from a direct local pathway when the one or more user devices 440 and 450 are in close physical proximity to the sensors 420, the home automation controls 422, the camera 430, the thermostat 434, and the robotic devices 490 to a pathway over network 405 when the one or more user devices 440 and 450 are farther from the sensors 420, the home automation controls 422, the camera 430, the thermostat 434, and the robotic devices 490. In some examples, the system leverages GPS information from the one or more user devices 440 and 450 to determine whether the one or more user devices 440 and 450 are close enough to the sensors 420, the home automation controls 422, the camera 430, the thermostat 434, and the robotic devices 490 to use the direct local pathway or whether the one or more user devices 440 and 450 are far enough from the sensors 420, the home automation controls 422, the camera 430, the thermostat 434, and the robotic devices 490 that the pathway over network 405 is required. In other examples, the system leverages status communications (e.g., pinging) between the one or more user devices 440 and 450 and the sensors 420, the home automation controls 422, the camera 430, the thermostat 434, and the robotic devices 490 to determine whether communication using the direct local pathway is possible. If communication using the direct local pathway is possible, the one or more user devices 440 and 450 communicate with the sensors 420, the home automation controls 422, the camera 430, the thermostat 434, and the robotic devices 490 using the direct local pathway. If communication using the direct local pathway is not possible, the one or more user devices 430 and 450 communicate with the sensors 420, the home automation controls 422, the camera 430, the thermostat 434, and the robotic devices 490 using the pathway over network 405.

In some implementations, the system 400 provides end users with access to images captured by the camera 430 to aid in decision making. The system 400 may transmit the images captured by the camera 430 over a wireless WAN network to the user devices 440 and 450. Because transmission over a wireless WAN network may be relatively expensive, the system 400 can use several techniques to reduce costs while providing access to significant levels of useful visual information (e.g., compressing data, down-sampling data, sending data only over inexpensive LAN connections, or other techniques).

In some implementations, a state of the monitoring system and other events sensed by the monitoring system may be used to enable/disable video/image recording devices (e.g., the camera 430). In these implementations, the camera 430 may be set to capture images on a periodic basis when the alarm system is armed in an "away" state, but set not to capture images when the alarm system is armed in a "home" state or disarmed. In addition, the camera 430 may be triggered to begin capturing images when the alarm system detects an event, such as an alarm event, a door-opening event for a door that leads to an area within a field of view of the camera 430, or motion in the area within the field of view of the camera 430. In other implementations, the camera 430 may capture images continuously, but the captured images may be stored or transmitted over a network when needed.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A computer-implemented method comprising:
detecting an increase in a level of particles within an area;
receiving data indicating a decrease in an air processing function of a heating, ventilation, and air conditioning (HVAC) system; and
automatically turning on an air purifier within the area based on:
i) the detected increase in the level of particles within the area; and
ii) the data indicating the decrease in the air processing function of the HVAC system.

2. The method of claim 1, comprising:
generating a notification based on: i) the detected increase in the level of particles within the area, and ii) the data indicating the decrease in the air processing function of the HVAC system; and
sending, to a user device, the notification indicating that an air filter needs to be changed.

3. The method of claim 2, comprising:
determining that the air filter has not been changed within a period of time after sending the notification; and
in response to determining that the air filter has not been changed within the period of time after sending the notification, automatically turning on the air purifier within the area.

4. The method of claim 2, comprising:
determining a type of the particles based on the detected increase in the level of particles within the area;
determining a type of the air filter based on the type of the particles; and
generating the notification indicating the type of the air filter prior to changing the air filter.

5. The method of claim 1, comprising:
determining that a room within the area has a higher level of volatile organic compounds than any other locations within the area; and
automatically turning on the air purifier in the room.

6. The method of claim 1, wherein the particles comprise one or more of: volatile organic compounds, pollens, and carbon monoxides.

7. The method of claim 1, comprising:
providing an instruction to the HVAC system to ventilate the area.

8. A system comprising one or more computers and one or more storage devices on which are stored instructions that are operable, when executed by the one or more computers, to cause the one or more computers to perform operations comprising:
detecting an increase in a level of particles within an area;
receiving data indicating a decrease in an air processing function of a heating, ventilation, and air conditioning (HVAC) system; and
automatically turning on an air purifier within the area based on:
i) the detected increase in the level of particles within the area; and
ii) the data indicating the decrease in the air processing function of the HVAC system.

9. The system of claim 8, the operations comprise:
generating a notification based on: i) the detected increase in the level of particles within the area, and ii) the data indicating the decrease in the air processing function of the HVAC system; and
sending, to a user device, the notification indicating that an air filter needs to be changed.

10. The system of claim 9, the operations comprise:
determining that the air filter has not been changed within a period of time after sending the notification; and
in response to determining that the air filter has not been changed within the period of time after sending the notification, automatically turning on the air purifier within the area.

11. The system of claim 9, the operations comprise:
determining a type of the particles based on the detected increase in the level of particles within the area;
determining a type of the air filter based on the type of the particles; and
generating the notification indicating the type of the air filter prior to changing the air filter.

12. The system of claim 8, the operations comprise:
determining that a room within the area has a higher level of volatile organic compounds than any other locations within the area; and
automatically turning on the air purifier in the room.

13. The system of claim 8, wherein the particles comprise one or more of: volatile organic compounds, pollens, and carbon monoxides.

14. The system of claim 8, the operations comprise:
providing an instruction to the HVAC system to ventilate the area.

15. A non-transitory computer-readable storage medium encoded with instructions that, when executed by one or more computers, cause the one or more computers to perform operations comprising:
detecting an increase in a level of particles within an area;
receiving data indicating a decrease in an air processing function of a heating, ventilation, and air conditioning (HVAC) system; and
automatically turning on an air purifier within the area based on:
i) the detected increase in the level of particles within the area; and
ii) the data indicating the decrease in the air processing function of the HVAC system.

16. The non-transitory computer-readable storage medium of claim 15, the operations comprise:
generating a notification based on: i) the detected increase in the level of particles within the area, and ii) the data indicating the decrease in the air processing function of the HVAC system; and
sending, to a user device, the notification indicating that an air filter needs to be changed.

17. The non-transitory computer-readable storage medium of claim 16, the operations comprise:
determining that the air filter has not been changed within a period of time after sending the notification; and
in response to determining that the air filter has not been changed within the period of time after sending the notification, automatically turning on the air purifier within the area.

18. The non-transitory computer-readable storage medium of claim 15, the operations comprise:
determining that a room within the area has a higher level of volatile organic compounds than any other locations within the area; and
automatically turning on the air purifier in the room.

19. The non-transitory computer-readable storage medium of claim 15, wherein the particles comprise one or more of: volatile organic compounds, pollens, and carbon monoxides.

20. The non-transitory computer-readable storage medium of claim 15, the operations comprise:
providing an instruction to the HVAC system to ventilate the area.

* * * * *